(12) United States Patent
Brunner et al.

(10) Patent No.: US 9,579,038 B2
(45) Date of Patent: Feb. 28, 2017

(54) ELECTRODE FOR A SCANNING ELECTRICAL IMPEDANCE TOMOGRAPHY DEVICE AND A SCANNING ELECTRICAL IMPEDANCE TOMOGRAPHY DEVICE

(75) Inventors: Josef X. Brunner, Chur (CH); Nicolas Robitaille, St. Augustin-de-Desmaures (CA); Pascal Olivier Gaggero, Biel (CH)

(73) Assignee: SWISSTOM AG (CH)

( * ) Notice: Subject to any disclaimer, the term of this patent is extended or adjusted under 35 U.S.C. 154(b) by 1057 days.

(21) Appl. No.: 13/635,094

(22) PCT Filed: Mar. 15, 2011

(86) PCT No.: PCT/CH2011/000051
§ 371 (c)(1),
(2), (4) Date: Dec. 17, 2012

(87) PCT Pub. No.: WO2011/113169
PCT Pub. Date: Sep. 22, 2011

(65) Prior Publication Data
US 2013/0217993 A1   Aug. 22, 2013

(30) Foreign Application Priority Data
Mar. 16, 2010  (CH) ...................... 0364/10

(51) Int. Cl.
*A61B 5/05* (2006.01)
*A61B 5/053* (2006.01)
(Continued)

(52) U.S. Cl.
CPC .... *A61B 5/0536* (2013.01); *A61B 2562/0209* (2013.01); *A61B 2562/043* (2013.01)

(58) Field of Classification Search
CPC ........ A61B 5/0536; A61B 5/053; A61B 5/063
(Continued)

(56) References Cited

U.S. PATENT DOCUMENTS 3,759,248 A * 9/1973 Valiquette ............ A61B 5/0436
600/516
4,140,997 A * 2/1979 Brady ................ A61B 5/04012
345/691
(Continued)

FOREIGN PATENT DOCUMENTS

DE    10156833 A1    5/2003
JP    5917329 A      1/1984

OTHER PUBLICATIONS

Guardo, R. et al., (Nov. 3, 1994). "Micro-controller based active electrodes for impedance tomography". Engineering in Medicine and biology Society, Engineering Advances: New Opportunities for Biomedical Engineers, Proceedings of the 16th Annual International Conference of the IEEE, Baltimore, MD, 545-546.
Rigaud, B. et al., (Nov. 1, 1993) "Experimental Acquisition System for Impedance Tomography With Active Electrode Approach". Medical and Biological Engineering and Computing, Springer, Heildelberg, DE, 31, (6), 593-599.
Williams, P. M., et al., (May 18, 1998) "Integrated electrodes for electrical capacitance tomography". Instrumentation and Measurement Technology Conference, Conference Proceedings IEEE, St. Paul, MN, 1, 472-475.
York, T. A. et al., (Jan. 9, 2003) "An intrinsically safe electrical tomography system". Industrial Electronics, IEEE International Symposium, Piscataway, NJ, 2, 946-951.
(Continued)

*Primary Examiner* — Joseph Stoklosa
*Assistant Examiner* — Brian M Antiskay
(74) *Attorney, Agent, or Firm* — Morriss O'Bryant Compagni, PC

(57) ABSTRACT

An electrode assembly for an EIT scanning device (11) including an electrode (15), a current supply unit (17), a voltage buffer unit (19), a switch logic unit (21), and lines for connecting the different elements, whereby the switch logic unit (21) comprises at least one element of a first shift register (27) and at least one element of a second shift register (29). A belt-like device comprising a plurality of said electrode assemblies. A method of measuring an EIT-image using such electrode assemblies preferably arranged in such a belt-like device.

15 Claims, 10 Drawing Sheets

(51) Int. Cl.
  *A61B 5/04* (2006.01)
  *A61B 5/02* (2006.01)
(58) Field of Classification Search
  USPC ........ 600/372–373, 382–388, 393, 407, 509,
  600/547, 506
  See application file for complete search history.

(56) References Cited

U.S. PATENT DOCUMENTS

| | | | |
|---|---|---|---|
| 4,193,393 A * | 3/1980 | Schlager | G01R 29/02 600/515 |
| 4,466,440 A * | 8/1984 | Money | H04B 14/062 327/91 |
| 4,617,939 A | 10/1986 | Brown et al. | |
| 5,626,146 A | 5/1997 | Barber | |
| 2005/0020935 A1 * | 1/2005 | Helzel et al. | 600/547 |
| 2005/0059901 A1 | 3/2005 | Garber et al. | |
| 2006/0004300 A1 * | 1/2006 | Kennedy | A61B 5/053 600/547 |
| 2008/0312522 A1 | 12/2008 | Rowlandson | |
| 2011/0087129 A1 * | 4/2011 | Chetham et al. | 600/547 |

OTHER PUBLICATIONS

York, T. A. et al., (Apr. 1, 2005) "Toward Process Tomography for Monitoring Pressure Filtration". IEEE Sensors Journal, IEEE Service Center, New York, NY, 5, (2), 139-152.

Costa, Eduardo L.V., (Feb. 2009) "Electrical impedance tomography." Current Opinion in Critical Care 15 (1):18-24. Lippincott Williams & Wilkins, United States.

Hansen, Christian (1998) Rank-deficient and discrete ill-posed problems : numerical aspects of linear inversion. Philadelphia: SIAM, p. 72.

Alder, A. and Guardo, R, Electrical impedance tomography: regularized imaging and contrast detection, IEEE Trans Med Imaging, 1996,15 170-179.

* cited by examiner

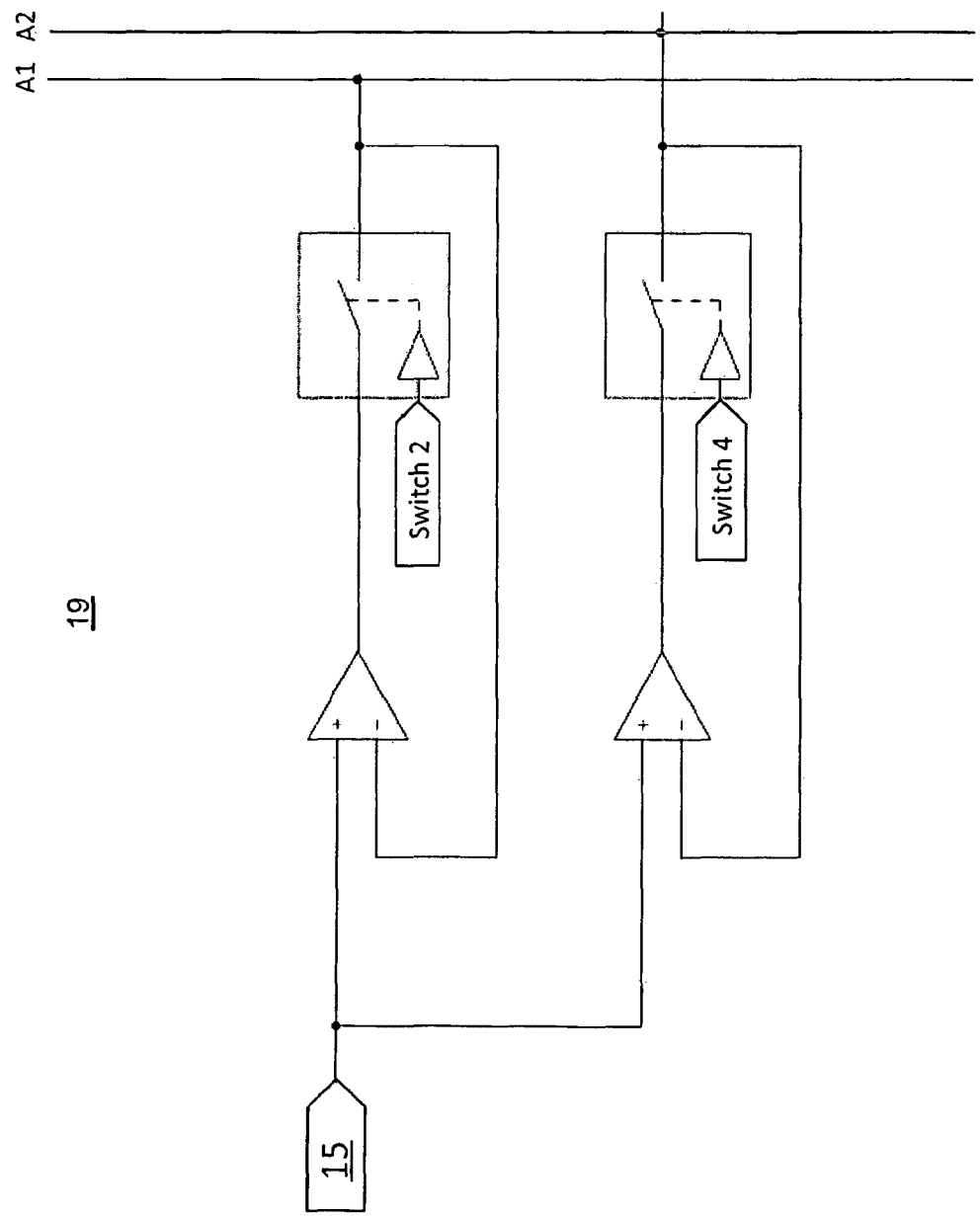

ELECTRODE FOR A SCANNING ELECTRICAL IMPEDANCE TOMOGRAPHY DEVICE AND A SCANNING ELECTRICAL IMPEDANCE TOMOGRAPHY DEVICE

CROSS-REFERENCE TO RELATED APPLICATIONS

This application is a national phase entry under 35 U.S.C. §371 of PCT/CH2011/000051 filed Mar. 15, 2011, which claims priority to Swiss Patent Application No. 364/10 filed Mar. 16, 2010, the entirety of each of which is incorporated by this reference.

BACKGROUND OF THE INVENTION

Field of the Invention

The present invention relates to an electrode assembly for an electrical impedance tomography (EIT) scanning device, a belt-like device comprising a plurality of said electrode assemblies and a method of measuring an electrical impedance tomography image using a plurality of electrode assemblies arranged in a spaced apart relationship.

Prior Art

Electrical impedance tomography (EIT) is a non-invasive imaging technique used to investigate and measure the composition and function of opaque bodies, including living species. Recently, EIT has been successfully applied in patients. For intensive care doctors, pulmonologists, and physiotherapists, electrical impedance tomography (EIT) is an imaging method that provides real-time information about regional lung ventilation and perfusion (flow of blood). In contrast to conventional methods, EIT does not require the patient to breathe through a sensor, does not apply ionizing x-rays, and can be used for extended periods, say 24 hours or even longer. Therefore, EIT can be used continuously and is therefore suited for monitoring treatment effects in real time and over time. EIT was first used to monitor respiratory function in 1983 and remains the only bedside method that allows continuous, non-invasive measurements of regional changes in lung volumes, blood flow, and cardiac activity. More details to this technique can be found in the article "Electrical impedance tomography" by Costa E L, Lima R G, Amato M B. in Curr Opin Crit Care. 2009 February; 15(1):18-24, which is incorporated herein by reference.

In EIT, as disclosed by U.S. Pat. No. 5,626,146, a plurality of electrodes, typically from 8 to 32, are arranged around the chest of a subject. A control unit ensures that an electrical signal, for example a current is applied to one or several pairs of electrodes on the skin to establish an electrical field which in turn is measured by the other electrodes. The electrodes used to apply current are called "current injecting electrodes" although one of them might serve as reference potential, for example ground. Typically, 3 to 10 mA are injected at 50 to 200 kHz. With the remaining electrodes, the resulting voltages are measured and subsequently used to estimate the distribution of electric impedance within the thorax. Specific algorithms were developed to convert the set of voltages into images. In order to overcome the ill-posed nature of impedance estimation, most EIT imaging algorithms make use of additional assumptions, known as a priori information and regularization. A priori information can be, for example, geometrical information about the subject chest. A typical regularization assumption is that intra-thoracic impedance distribution shall have no abrupt changes. Another assumption is that all electrodes are properly connected to the skin of the patient. The resulting images provide a reasonable estimation of the true impedance distribution within the thorax.

To be useful for the user, for example the clinician, the calculated impedance-distribution image is converted into an image that shows presence of air, absence of air, or changes of air content, changes of blood content, and/or muscular excursion into body spaces. Instead of air, any breathable gas mixture can be used in EIT. Plotted rapidly in sequence, several times per second and like a movie, these images create a visual representation of gas and blood flow in and out of each lung region and allow the doctor to evaluate lung function and/or cardiac function in real-time. Current main obstacles to wide spread use of EIT are poor reliability and high cost.

Electrodes can disconnect easily and electrical contact with the skin may vary by orders of magnitude, from as much as 500 Ohms to 10,000 Ohms. Poorly connected electrodes are unable to inject the necessary pre-defined current due to voltage supply limits. Consequently, the resulting images often contain artefacts due to in-homogeneous current injection. Such artefacts can be mistaken as physiologic signals and potentially lead to wrong diagnosis and inappropriate therapy. An example of artefacts due to bad electrode contact is given in FIG. 6b. Even though the user may know that the electrodes make bad contact, he/she might not know what appropriate corrective action might be done.

Rigaud et al. describe in the article "Experimental acquisition system for impedance tomography with active electrode approach" (in Med Biol Eng&Comput, November 1993, 31:593-599) an experimental EIT measuring system comprising an acquisition system including a plurality of so-called "active electrodes" and a control unit including a reference voltage source and an acquisition circuit. The active electrodes comprise each a voltage buffer, a set of switches and a switch logic unit, controlled by the acquisition system. Close to the electrode a current source, the voltage buffer and the set of switches are connected. By these means the electrodes become multifunctional.

In Rigaud the switch logic units of the electrodes are connected to data lines in parallel. Thus each electrode needs appropriate addressing, digital storage, and synchronization. As each electrode must have a unique address, a programmable microchip or special hardwired addressing must be used for this purpose. This makes the manufacture of the control circuitry for the electrodes costly.

The solution proposed by Rigaud assumes that all electrodes are always working well. In their paper, there is no provision disclosed to check the proper function of the electrodes. Also, there is no mention of a method to identify electrodes that are not in good contact with the skin. Non properly functioning electrodes or electrodes with a poor skin contact however have a detrimental effect on the results and should therefore be accounted for.

In Rigaud the differential voltage of two electrodes is hard-wired to a hardware demodulator with subsequent low pass filter. This has the advantage that demodulation is quick. The disadvantage is that the hardware implementation of the analog demodulator is costly and less flexible.

The apparatus disclosed by Rigaud contains as many current sources as electrodes. These current sources are switched on and off by a central computer. Theoretically and practically, more than one current source can be active at the same time thereby injecting potentially life threatening levels of current. Rigaud does not disclose any method to prevent the simultaneous injection of currents in their distributed electrode arrangement.

In one implementation of an intrinsically safe EIT for the purpose of monitoring progress during pressure filtration, as disclosed by York et al. in "An Intrinsically Safe Electrical Tomography System", Industrial Electronics, 2003, ISIE '03, 2003 IEEE International Symposium on 9-11 Jun. 2003, vol. 2, pages 946-951, and/or in "Towards Process Tomography for Monitoring Pressure Filtration", IEEE Sensors Journal, vol. 5, no. 2, April 2005, a plurality of electrodes, typically between 16 and 24, are arranged around the subject of interest, in this case said subject of interest is a vessel for pressure filtration in a chemical plant for the separation of a liquid from a solid phase. In this apparatus according to York et al four relays are dedicated to control the electrical signals of any given electrode, one to connect the electrode to the positive line of the current source, one to connect to the negative line of the current source, one to connect to the positive line of the voltmeter, and one to connect to the negative line of a voltmeter. Control of these 4 relays is done by arranging them as one single-bit shift register in a daisy chain and controlling the daisy chain with a connected PC. The mentioned slowness of the measurements, i.e. a rate of about 1-2 images per minute, signifies no disadvantage for the purpose of monitoring pressure filtration processes. Although it is stated that the EIT system described by York et al could be readily applied to other purposes besides the monitoring of progress during pressure filtration, a number of problems would arise if said system were applied for medical purposes. Some of the reasons are as follows: (a) the huge distance between the amplifiers for measuring the voltages and the electrodes, typically 50 meters, creates problems with regard to interference and noise; (b) the low image rate is not acceptable, because the changes in a living body occur with a much faster rate (e.g. breathing or heartbeat rate); and (c) the life time of the electromechanical relays used by York is limited, typically 5 million cycles, due to mechanical use of the parts, which is not acceptable for medical measurements.

US application 2005/0059901 A1 discloses a method to improve reliability of measurement in the frequency domain. The method proposes to search for a frequency of the injection current that provides an optimal signal to noise ratio. It does not take into account that an electrode may fail to make contact with the skin. The said disclosed method will therefore not work if electrodes do not make contact with the skin.

It is known that contact impedance can be calculated as the quotient of the measured voltage and current. However, such measurement does not help to decide when an electrode makes sufficient contact to obtain reliable EIT images. Comparison with expected impedance does not help either since the current injecting device may be beyond its range of operation and thus induce measurement artefacts.

It has been suggested to display the failing electrode on a graphical user interface and/or to trigger an alarm sound to make the user aware of the situation. Neither of these measures prevents the calculation of potentially misleading images.

Another disadvantage of current EIT systems is the high cost. EIT systems measure the voltages for each electrode separately to average the noise inherent in the measurements. Such implementation is rather expensive since it requires as many measurement channels as there are electrodes. A much less expensive implementation would be to measure the voltages around the chest one by one, i.e. employ multiplexing. This technique is known in the art and allows the sharing of significant resources such as expensive differential amplifiers and fast analog-to-digital converters. However, there is significant noise in the measurements that can be eliminated by averaging. For this reason it is advantageous to maximize measurement time. For example, if one of the electrodes is failing, the time allocated for such failing electrode is completely wasted. It would be of great advantage to have a method to exclude non-functioning electrodes from the measurement sequence in order to maximize the time for the functioning electrodes.

A device that is able to provide reliable EIT images in presence of non-contacting electrodes has not been described and is thus currently not available. For the reasons described above, there is a clear need for such robust device to avoid misinterpretation of images and inappropriate therapy.

Accordingly, it is an advantage of the present invention to provide a reliable electrode assembly which can be manufactured at low costs. Another advantage is to provide an assembly circuit for an electrode which does not require prior addressing and expensive electronic parts. A still further advantage is to propose a device and a method by which non-functioning electrodes can be excluded from the measurement sequence. Another advantage is to provide a device and a method that create reliable EIT images in presence of erroneous data due to non-functioning or poorly functioning electrodes. Another advantage is to provide a device and a method that create reliable EIT images for the purpose of medical examination, particularly of lung and heart. Another advantage is to increase the versatility of EIT method, in particular for medical examination. Furthermore another advantage is to independently control the patterns of current injection and the patterns of voltage readout.

SUMMARY OF THE INVENTION

The foregoing advantages are provided with the inventive electrode and belt-like device according to the principles of the present invention.

The inventive electrode assembly for an EIT scanning device including
- an electrode,
- a current supply unit,
- a voltage buffer unit,
- a switch logic unit,
- lines for connecting the current supply unit and the voltage buffer unit with the electrode,
- lines for connecting the current supply unit and the voltage buffer unit with the switch logic unit, and
- the switch logic unit being in contact with switches for actuating the current supply unit and the voltage buffer unit in accordance with, i.e. based on, data received from the switch logic unit,
- the switch logic unit comprises at least one element of a first shift register and at least one element of a second shift register.

Advantageously, this electrode assembly construction allows for a sequential activation of a plurality of electrodes, which are for example aligned on a belt-like structure. There is no need to provide each electrode with a specific address through which the electrode is addressed by a microprocessor. Without individual address the manufacturing costs of the electrode drivers may be kept low. Therefore a production of disposable electrodes and belt-like structures is rendered possible.

With at least two shift register elements of which one element being part of a first shift register (i.e. of a first daisy chain) and one element being part of a second shift register (i.e. of a second daisy chain), the switch logic unit allows to advance two different command structures in different intervals. This leading to the advantageous situation that according to the present invention a first current injecting command structure is triggered at a first interval and a second measurement command structure is triggered at a second, faster interval, enabling many measurements during a specific current application configuration.

The monitoring of different regions of interest in the human body might require different current injection and voltage readout patterns. To monitor the heart which is located in close proximity to the anterior chest wall, for example, it is advantageous to primarily apply current injection to the vicinity of the heart and not inject current in the dorsal parts. At the same time, the resulting voltages should be measured using all electrodes. This is possible due to an electrode assembly design having at least two shift registers. In comparison only one pattern of current injection and voltage reading can be moved through a single shift register (i.e. through one daisy chain).

A double shift register arrangement makes measurements more time efficient, where faulty electrodes are present. If one electrode fails, it is advantageous to quickly cycle through this failing electrode, thereby effectively skip it and move the measurements on to the next electrodes without switching the current injecting electrode. This becomes possible with the two shift register arrangement according to present invention. Contrary thereto in the known device according to York et al as cited above the entire scanning pattern has to be re-loaded again and again. At the same time a higher amount of the measured values are faulty.

The inventive double shift register arrangement of the electrode assembly is much faster (typically one thousand times faster) than conventional systems using electro-mechanical relays, which result typically in one image frame every 30 second for a 16-electrode system.

The at least one element of a first shift register and said at least one element of a second shift register (i.e. the elements of a shift register) may be controlled by two different clocks, clock rates and/or clock lines.

The at least one element of a first shift register and said at least one element of a second shift register may be located in close proximity to the electrode, for example not more than one centimeter away and directly on the electrode.

The at least one element of a shift register may be a flip-flop. Likewise, the at least one element of a shift register may be a 2-bit flip-flop. The 2-bit flip-flop allows to allot up to four different settings in a command structure. Advantageously the 2-bit flip-flop is composed of two parallel flip-flops, in particular two edge triggered D-flip-flops or two master slave flip-flops.

The switch logic unit may comprise the at least one element of a first shift register, e.g. a flip-flop, for connecting the current supply unit with the electrode via at least a first switch, and the at least one element of a second shift register, e.g. a flip-flop, for connecting the voltage buffer unit with analog lines A1 and A2 via at least a second switch.

A third switch may be controlled by the at least one element of the first shift register for connecting the electrode with a reference potential, for example ground or any other voltage level that is deemed necessary and is provided by the device. This ground does not have to be a constant voltage. It could, for example, also be an alternating voltage.

The at least one element of a first shift register (e.g. a 2-bit flip-flop) may be connected with the first and third switch. Hereby the injecting current circuit can be closed between injection source and reference voltage, for example ground, over any selected pair of electrodes.

The voltage buffer unit may comprise a first and a second voltage buffer and said second switch and a fourth switch for connecting one of or both of the first and second voltage buffers to the respective first and second analog lines A1 and A2. Hereby the voltage difference and consequently the voltage can be measured between any selected pair of electrodes.

The at least one element of a second shift register (e.g. a 2-bit flip-flop) may be connected with the second and fourth switch.

The individual switch actuation has the advantage that different measurement patterns may be implemented. One pattern is the measurement of the voltage drop between pairs of electrodes in a clockwise or counter-clockwise manner. The pairs of electrodes are at least 60 degrees apart from each other when measured as angle from the centre of a circle in the measurement plain. In any case, the pairs of electrodes may be for example pairs of adjacent electrodes.

It is particularly advantageous to be able to choose the current injection pattern, which may be different from the voltage readout sequence. One important use is the exclusion of faulty electrodes from the measurements and re-allocating the time saved for measurements on the properly functioning electrodes. Another use of the inventive assembly it is to focus the analysis on certain organs, for example the heart. Current injection is focused on electrodes which are close to the heart while the measurements of all electrodes are taken into account. Yet another use it is to measure different voltage patterns in subsequent scans at one given current injection pattern. Such a second measurement scan creates an essentially independent set of measurements which is helpful for noise reduction procedures in later stages of the analysis.

A further or a fifth switch may be provided for connecting a reference signal line, typically a sinus wave, with the current supply unit. The setting of the fifth switch (which in fact corresponds to the setting of the first switch) determines whether a sinus wave is applied to a selected electrode. The sinus wave determines the amplitude and frequency of the injecting current. The frequency of the sinus wave constitutes the selected frequency of the voltage measurement.

The current supply unit, the voltage buffer unit, the at least one element of a first shift register, the at least one element of a second shift register and/or the switches may be integrated in an integrated circuit, i.e. designed as an integrated circuit. The elements of the shift registers (i.e. at least the at least one element of a first shift register and the at least one element of a second shift register) may be integrated in an integrated circuit. Such integrated circuits are small enough to be mounted on or in close vicinity of each electrode.

The integrated circuit may be arranged on or attached to the electrode. This allows for an optimally compact design of a belt-like arrangement comprising a plurality of electrode assemblies.

Advantageously there is a safety unit, e.g. a comparator circuitry, provided, which is in connection with a second current source, for measuring the voltage drop across said second current source. The safety circuitry has a control function which allows to prevent situations, where the injected current (i.e. the sum of all current passing through the tested sample or body) increases above a predetermined maximal threshold level. Dangerously high injection current levels are thus avoided.

The safety unit may comprise at least a resistor and a switch, with the switch being in contact with the switch logic unit and the switch being controllable to connect the second current source to ground via the resistor whenever the electrode is acting as injecting electrode.

The voltages measured may be converted to digital format before the demodulation. Thus, the A/D conversion occurs before the demodulation. This has the advantage that the measured signal may be analysed and evaluated directly without modification prior to demodulation.

An alternative inventive electrode assembly for an EIT scanning device includes
  an electrode,
  a current supply unit,
  a voltage buffer unit,
  a switch logic unit,
  lines for connecting the current supply unit and the voltage buffer unit with the electrode,
  lines for connecting the current supply unit and the voltage buffer unit with the switch logic unit,
  the switch logic unit being in contact with switches for actuating the current supply unit and the voltage buffer unit in accordance with data received from the switch logic unit, and
  a safety unit, for example a comparator circuitry, is provided, which is in connection with a second current source, for measuring the voltage drop across said second current source.

Advantageously this electrode assembly when used in combination with a plurality of identical electrode assemblies allows safe execution of EIT measurements by injecting current through one injecting electrode at a time only. If due to some error several electrodes act as injecting electrodes the exposure of a patient to current risks to become too high. In this instance the voltage drop across the second current source decreases below a predetermined threshold level. At this moment switches of the safety circuitry are activated and all current injection is stopped as a precautionary measure.

The switch logic unit may comprise at least one element of a first shift register, e.g. a flip-flop, and at least one element of a second shift register, e.g. a flip-flop.

This alternative electrode assembly may comprise alone or in combination any one of the features disclosed herein with regard to any other electrode assembly.

The inventive belt-like device may comprise a plurality of said electrode assemblies being arranged in a spaced apart relationship on a supporting strap element, said supporting strap element comprising also connecting lines for connecting the current supply units, the voltage buffer units and the switch logic units of the electrode assemblies with a control circuit. Such belt-like device may be manufactured inexpensively. And therefore may be used as disposable device.

The switch logic units of neighboring electrode assemblies are connected in series with each other.

The current supply units and the voltage buffer units of different electrode assemblies may be connected with each other in parallel.

The belt-like device may be provided with a safety connection line connecting a second current source with all electrodes for detecting simultaneous current injection by multiple injecting current sources. The safety line has a control function which allows to prevent situations, where the injected current increases above a predetermined maximal threshold level. Dangerously high injection current levels are thus avoided.

The control circuit which may be provided comprises a scanning unit, a measurement unit, a support function unit, and a computing unit, said units being in contact with the electrodes via the connecting lines.

The measurement unit may comprise first and second differential amplifiers and first and second A/D converters being connected to said first and second differential amplifiers. Hereby one amplifier is capable of measuring small voltage differences accurately and the other amplifier is capable of measuring high voltage differences accurately. Due to the relative good conductivity of an examined sample, i.e. a body, usually small voltage differences are expected and for example measured with the first amplifier, which e.g. has relatively high gain. However, if one or both electrodes of a pair are defective the expected voltage difference is high and can be determined reliably by the second amplifier, which e.g. has relatively low gain.

The first and second differential amplifiers may comprise two different gains, with the first amplifier has a gain in the range of 100 to 1000 and the second amplifier has a gain in the range of 1 to 100.

The scanning unit may be designed for providing data signals for controlling the at least one element of a first shift register and the at least one element of a second shift register and clock signals for clocking the at least one element of a first shift register and the at least one element of a second shift register.

The at least one element of a first shift register and the at least one element of a second shift register may be clocked in two different intervals. Consequently, the switch logic unit can trigger two different command structures in different intervals.

The support function unit may be designed for providing the supply voltage and the reference signal for the injecting current source.

The support function unit may be designed for providing the supply voltage, the reference signal, and an excitation signal for the injecting current source.

The computing unit may be connected to the measurement unit and being designed for computing the desired EIT scanning image using the data received from the measuring unit.

The inventive EIT scanning system comprises a belt-like device as described above and an image calculation device being connected to the control circuit.

The inventive method of measuring an EIT-image comprising the use of a plurality of electrode assemblies being arranged in a spaced apart relationship each electrode assembly comprising
  an electrode,
  a current supply unit,
  a voltage buffer unit,
  a switch logic unit,
  lines for connecting the current supply unit and the voltage buffer unit with the electrode,
  lines for connecting the current supply unit and the voltage buffer unit, with the switch logic unit,
  the switch logic unit being in contact with switches for actuating the current supply unit and the voltage buffer unit in accordance with data received from the switch logic unit,
  and the electrode assemblies being connected by connecting lines for connecting the current supply units, the voltage buffer units and the switch logic units with a control circuit, wherein the switch logic is controlled with at least one element of a first shift register (27) and at least one element of a second shift register (29). Optionally said method further comprises current injection by the electrodes controlled by a safety circuitry for preventing simultaneous current injection via more than one electrode at a time.

According to an alternative embodiment an inventive method of measuring an EIT-image comprises
the use of a plurality of electrode assemblies being arranged in a spaced apart relationship
each electrode assembly comprising
an electrode,
a current supply unit,
a voltage buffer unit,
a switch logic unit,
lines for connecting the current supply unit and the voltage buffer unit with the electrode,
lines for connecting the current supply unit and the voltage buffer unit, with the switch logic unit, and
the switch logic unit being in contact with switches for actuating the current supply unit and the voltage buffer unit in accordance with data received from the switch logic unit,
and the electrode assemblies being connected by connecting lines for connecting the current supply units, the voltage buffer units and the switch logic units with a control circuit, wherein current injection by the electrodes is controlled by a safety circuitry for preventing simultaneous current injection via more than one electrode at a time. Optionally said method is further characterized in that the switch logic is controlled with at least one element of a first shift register (27) and at least one element of a second shift register (29).

Both said methods enable a safe and secure application of the EIT measurement. The switch logic allows the control of the measurement in such a way that at a time one single electrode acts as injecting electrode. The safety circuitry provides an additional security to ensure that all current injection is stopped if due to a faulty electrode assembly or control circuit more than one electrodes act simultaneously as current injecting electrodes.

The first shift register (27) and said second shift register (29) may be controlled by a different clock, different clock rate or different clock line.

The safety circuitry may comprise a safety unit (22) as described above.

The safety unit may comprise at least a resistor and a switch, with the switch being in contact with the switch logic unit and the switch being controllable to connect the second current source to the resistor whenever the electrode is acting as injecting electrode.

BRIEF DESCRIPTION OF THE DRAWINGS

FIG. 4 illustrates the voltage buffer unit with first and second voltage buffers and command switches for connecting the voltage buffers with analog sampling lines A1 and A2;

DETAILED DESCRIPTION OF THE ILLUSTRATED EMBODIMENTS

Figure 1:
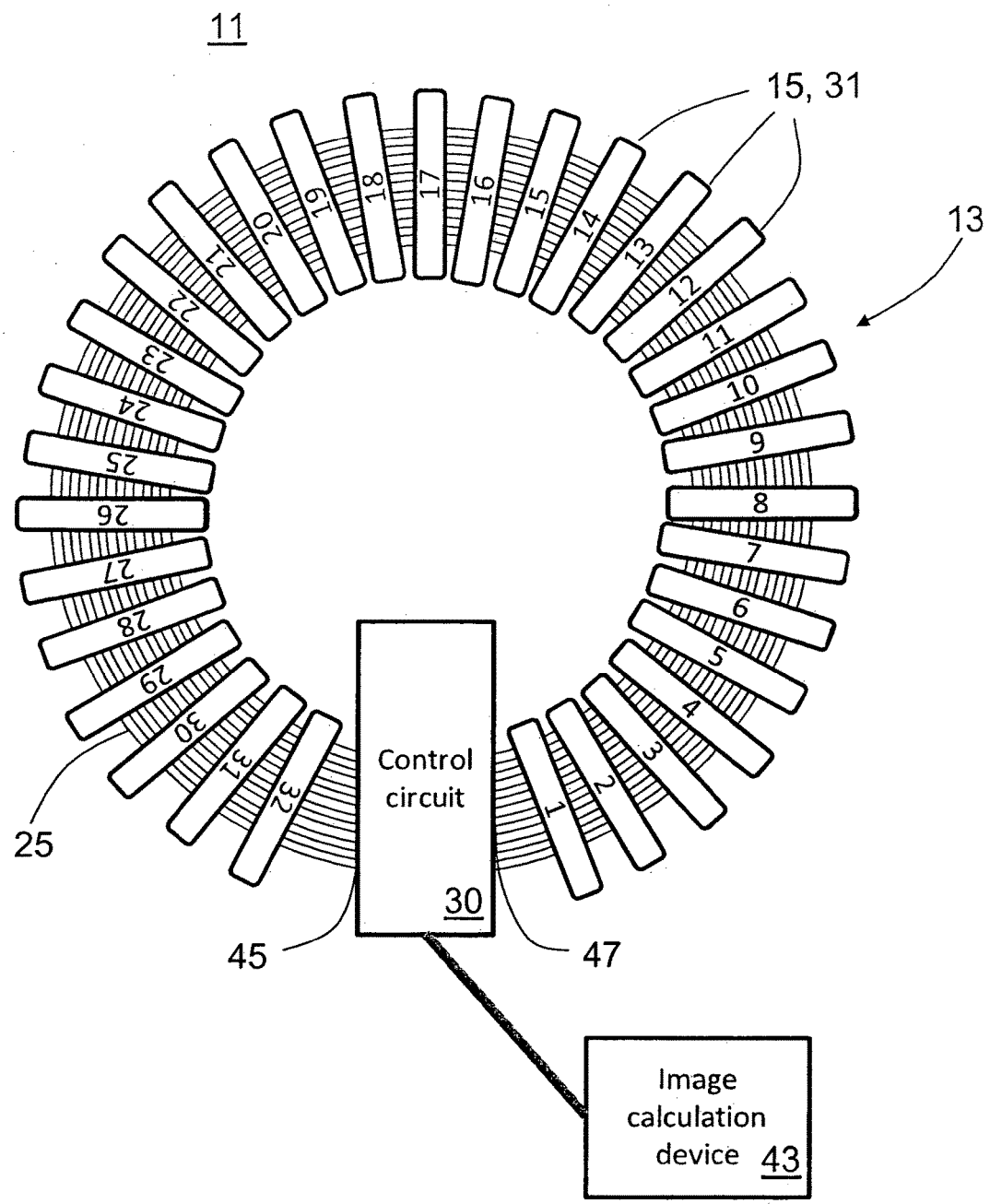
FIG. 1 illustrates schematically, an inventive EIT scanning system comprising 32 single electrodes connected with each other via a bus system, including data and analog lines, and a control circuit, which may be part of the sensor belt or releasable connected therewith, and an image calculation device connected to the control circuit.

As in any conventional EIT system, current is injected to establish an electrical field and this field is subsequently measured by a plurality of electrodes placed around the chest. To obtain maximal flexibility, each electrode can be used to inject current. In an arrangement of 8 electrodes, for example, this leads to 8 different locations of current injection and 8 measurements for each location of current injection. Typically, a total of 8 times 8=64 measurements will result, called measurement vector b in the following chapters. Alternatively, with other scanning patterns, more or less measurements can result.

In the present invention, a plurality of electrodes is arranged on a belt-like structure around the thorax of a patient. Both ends of such a belt join in a connector, either at fixed or variable length. The connector measures the stretch of the belt, for example with a strain gauge. The stretching force of the belt-like structure is subsequently provided to the user advantageously together with the information about any poorly contacting electrodes. The latter is measured as follows:

A plurality of current sources mounted on the same belt-like structure around the patient's chest apply AC current between 1 and 10 mA RMS, or 5 and 10 mA RMS, at frequencies between 50 kHz and 200 kHz. The injecting current sources are voltage controlled high output impedance current sources. One of the electrodes acts as ground electrode, reference potential, or current sink. To drive the current through the variable contact impedance between electrode and skin, each current source is working in a closed-loop control mode. As a result, the output voltage will vary to accommodate different and time-varying electrode-skin impedances. In normal operation, this voltage will typically be below 50% of the supply voltage. If the current source is unable to drive the pre-set current through the body, it will output a voltage that is close to the supply voltage, typically higher than 80% of the supply voltage. According to an aspect of the invention all voltages on all electrodes are measured in a first full scan of all electrodes. For this purpose, the voltage buffers placed on the electrodes can be used. They pass the measured voltages on to an analog measurement unit which determines according to the measured voltage whether a specific electrode is properly functioning or not.

If, for example, 8 electrodes are placed around the chest, 8 measurements will be needed to assess the contact quality of each electrode. If an electrode is not in sufficient contact with the skin, the corresponding current source is unable to drive the set current through the body and the voltage at the electrode will approach the supply voltage. The same applies if the corresponding current sink (reference potential) electrode is not making good contact. Thus, if the measured voltage is higher than a certain threshold, typically 80% of the supply voltage, across a given electrode pair, one of the two electrodes can be designated as non-functional. The said threshold is independent of the body to be examined. It is independent of the electrode-to-skin impedance, and only a function of the power supply capabilities. Since it is not clear which one of two electrodes, or possibly both electrodes, caused the high voltage measurement and thus do not make good contact, the assessment procedure has to be repeated with both electrodes connected to an independent electrode. Such a procedure is implicit in a typical EIT scan, i.e. where the two current injecting electrodes are moved around the body in a round-robin pattern, either being electrodes that are adjacent or skip any number of electrodes between the two electrodes to be measured. Thus it is possible to sort out all the non-properly functioning electrodes at the beginning of the EIT-measurement. Each electrode that resulted two times in bad contact can safely be designated as "non-functional". In a next step, all values measured with the non-functional electrodes are excluded from further analysis.

To prevent accidental injection of AC current through multiple current sources, an optional safety connection is implemented. This safety connection is supplied by a separate DC or AC current source of typically 2 mA (compare FIG. 7). On each electrode, the switch that controls the on-board AC current source can be connected with another switch that connects a resistor of e.g. 1 kOhm to the safety line (FIG. 5). If the function of the electrode is to inject AC current, this second switch connects the resistor to the safety connection and thereby drains all the DC current. If, by accident, a second electrode would try to inject AC current at the same time, the DC current would also be diverted by this second electrode. As a result, the voltage of the safety connection would drop by 50%, for example from 2 Volts to 1 Volt. The central control unit is designed to check this voltage and, if the voltage drops to 1 Volt or less, switches off the supply to all the electrodes thereby preventing the injection of dangerously high AC currents.

The problem of reconstructing an impedance map of a body section is solved by using the Finite Element Method (FEM), a technique known in the art. The FEM uses a mesh of triangles to describe the space or surface of interest, then the physics of the problem is applied to the mesh and the problem is solved by using certain boundary conditions (i.e. since it is not possible to extend the mesh to an infinite space, one has to restrain the mesh to the studied medium of interests and describe what happens at the boundary of the mesh).

The forward problem of EIT is to compute the potentials at the voltage measuring electrodes, for a given set of current injection electrodes and a given conductivity distribution.

Typically, the reconstruction problem is solved for the EIT forward problem by $Y(s)*V=C$, where Y is the conductance matrix, depending on the conductivity s, V is a set of voltage distribution and C is a set of applied currents.

Given that one can only measure the voltage at the medium boundary at given places (i.e. at the electrodes) the operator D is introduced. It returns a vector of voltage measurements corresponding to a given system and scanning pattern, $$v=D(V)=Y^{-1}*C.$$

The above forward problem is then linearized with respect to a reference conductivity $s_0$ using Taylor expansion, $$\Delta v = S\Delta\sigma,$$

where S is the sensitivity matrix $$\left.\frac{\delta v}{\delta \sigma}\right|_{\sigma_o},$$

$\Delta\sigma$ is $s-s_0$
and $\Delta v$ is $v-v_0$.

For a given change in the measurements $\Delta v$, we thus obtain a change in conductivity $\Delta\sigma$. In the image reconstruction process, the idea is to find the change in conductivity $\Delta\sigma$ from a given change in the measurements $\Delta v$.

To compute $\Delta\sigma$ one has to inverse the matrix S. This operation is in general non-trivial and cannot be performed using the classical inverse of a matrix. This category of problem is know in the literature has inverse ill-posed problems. This means that the problem has more unknowns than equations. A way to calculate solutions, despite the ill-posed nature, is to use a regularization technique which implies that some assumptions are made over the medium of interest. The idea in EIT is essentially to find a least-square solution $\Delta\sigma$ of the problem ($\|S\Delta\sigma - \Delta v\|^2$). Since the problem is ill-posed, a regularization term is added yielding the following cost function (see, for example, Adler and Guardo, 1996):

$$\Phi = \frac{1}{2}\|S\Delta\sigma - \Delta v\|^2 + \frac{\lambda}{2}\|F\Delta\sigma\|,$$

where $\lambda$ is the weighting term of the regularization term and F is a spatial high-pass filter matrix.

One can note that the use of the Euclidian norm (squared) is not mandatory; another norm can also be used.

The idea is then to minimize this cost function and find a solution for $\Delta\sigma$. Here one can solve the problem using the Singular Value Decomposition (SVD) methodology. The regularized solution for the above given cost function is given for the standard form in (Hansen, Rank-deficient and discrete ill-posed problems, 1998, SIAM, ISBN-978-0-898714-03-6, page 72). We first transform our cost function to get the standard-form expression:

$$\Phi = \frac{1}{2}\|Ax - b\|^2 + \frac{\lambda}{2}\|x\|, \quad \text{(Equation I)}$$

where $x = F \Delta\sigma$,
$b = \Delta v$.

The pseudo-inverse is used to calculate $\Delta\sigma$:

$$\Delta\sigma = F^{\#}x = [F^TF]^{-1}F^Tx = Lx \quad \text{(Equation II)}$$

One then rewrites the cost function as follows:

$$\Phi = \frac{1}{2}\|SLx - b\|^2 + \frac{\lambda}{2}\|x\|,$$

A is then SL.

$$A = \frac{SL}{\sqrt{\|s\|_{frobenius}}}$$

The SVD of A is $$A = U\Sigma V^T,$$

where $UU^T = I$, $VV^T = I$ and S is a diagonal matrix containing the singular values.

Hansen gives us the solution for such regularization problems:

$$x = V\Theta[\Sigma^T\Sigma]^{-1}\Sigma^T U^T b.$$

One can rewrite the above expression:

$$x = VEU^T b,$$

where $$[E]_{ii} = \frac{\sigma_i}{\sigma_i^2 + \lambda},$$

and $s_i$ are the singular values.

Thus, by using Equation II the regularized solution of $\Delta\sigma$ becomes $$\Delta\sigma = MED\Delta v,$$

Where $$M = \frac{LV}{\sqrt{\|s\|_{frobenius}}}$$

$$D = U^T,$$

$$[E]_{ii} = \frac{\sigma_i}{\sigma_i^2 + \lambda}$$

At this stage the reconstruction matrix MED can be calculated almost on-the-fly by multiplying the 3 basis matrices M, E and D, and by changing the regularization λ factor in E. This allows the EIT system to adapt the regularization term to obtain the required image quality.

One way to find the optimal λ factor could be the L-curve method as described in (Hansen, 1998).

According to one embodiment it is advantageous to exclude data coming from a given subset of electrodes, which is for example non-functioning or erroneous. For this purpose the above calculation is repeated by restarting the calculation procedure at Equation 1 and by removing the matrix lines of A and b of the voltage measurements corresponding to the rejected electrodes. The rest of the procedure is exactly the same as described above.

Figure 2:
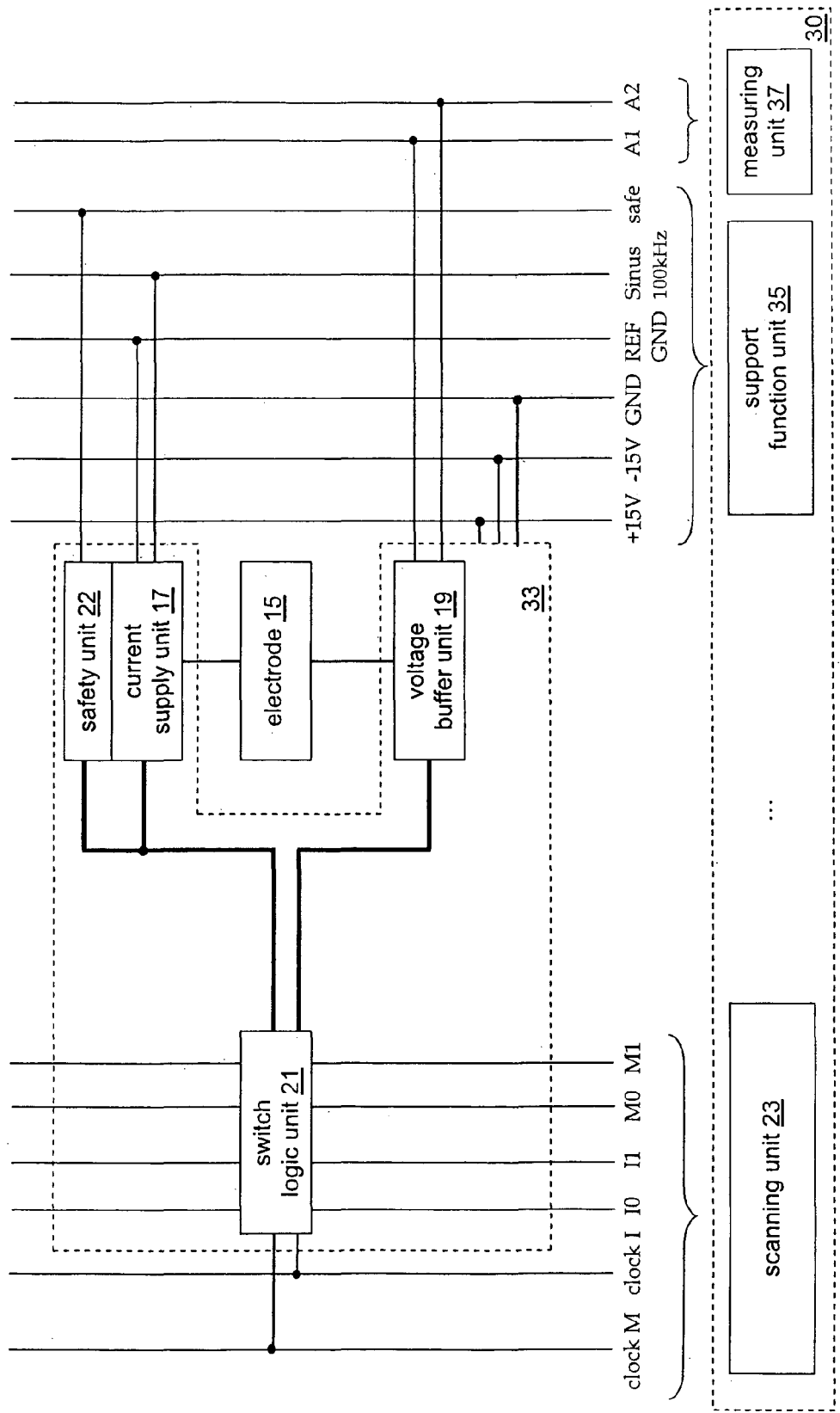
FIG. 2 illustrates schematically an electrode driving unit comprising a current supply unit, a voltage buffer unit and a switch logic unit.

The invention is hereinafter described with reference to the figures. They show in The EIT scanning system 11 of FIG. 1 comprises a plurality of electrodes 15, typically between 8 to 32, which can be arranged on the surface of a human body to be examined, for example a human chest. Each electrode 15 is mounted on a belt 13 so that the user can conveniently place the electrodes 15 around the patient's chest. As shown in FIG. 2 in close vicinity of each electrode 15 are placed an injecting current supply unit 17, a voltage buffer unit 19, and a switch logic unit 21 and an optional safety unit 22. Hereby, the assembly of an electrode 15, a current supply unit 17, a voltage buffer unit 19 and a switch logic unit 21 constitutes an electrode driver or assembly 31. An electrode driver 31 is designed as an electrode 15 with integrated electronics 33, i.e. integrated circuit. The electrode drivers 31 are controlled by an external control circuit 30 (FIGS. 1 and 2). The injecting current supply units 17 are based on a voltage controlled high output impedance current source. The current supply units 17 apply currents between 5 and 10 mA RMS at frequencies typically between 50 kHz and 200 kHz. Higher or lower frequencies are also possible. The voltage buffer units 19 measure the voltage directly at each electrode 15 and pass this voltage on to a bus system 25 which is laid around the thorax of the subject, e.g. a patient, and which connects all electrode drivers 31 with the control circuit 30.

As shown in FIG. 2, the external control circuit 30 communicates with each electrode 15 and its integrated electronics 33 via a composite bus 25, consisting of digital communication data lines I0, I1, M0, and M1 and analog signal lines A1, A2. The control circuit 30 can also contain a sensor to measure the force exerted by the belt (not shown in the figures). This sensor is a strain gauge that mechanically connects to both arms or ends 45, 47 of the sensor belt 13 connected to the control circuit box 30.

FIG. 1 shows the principle design in its embodiment for a 32 electrode arrangement. All electrodes are connected via data bus lines I0, I1, M0, and M1 and analog bus lines A1 and A2. By the data transferred by the said bus lines the function of each electrode can be determined. In one embodiment, the data bus is implemented as a daisy chain running from one electrode to the next.

Figure 5A:
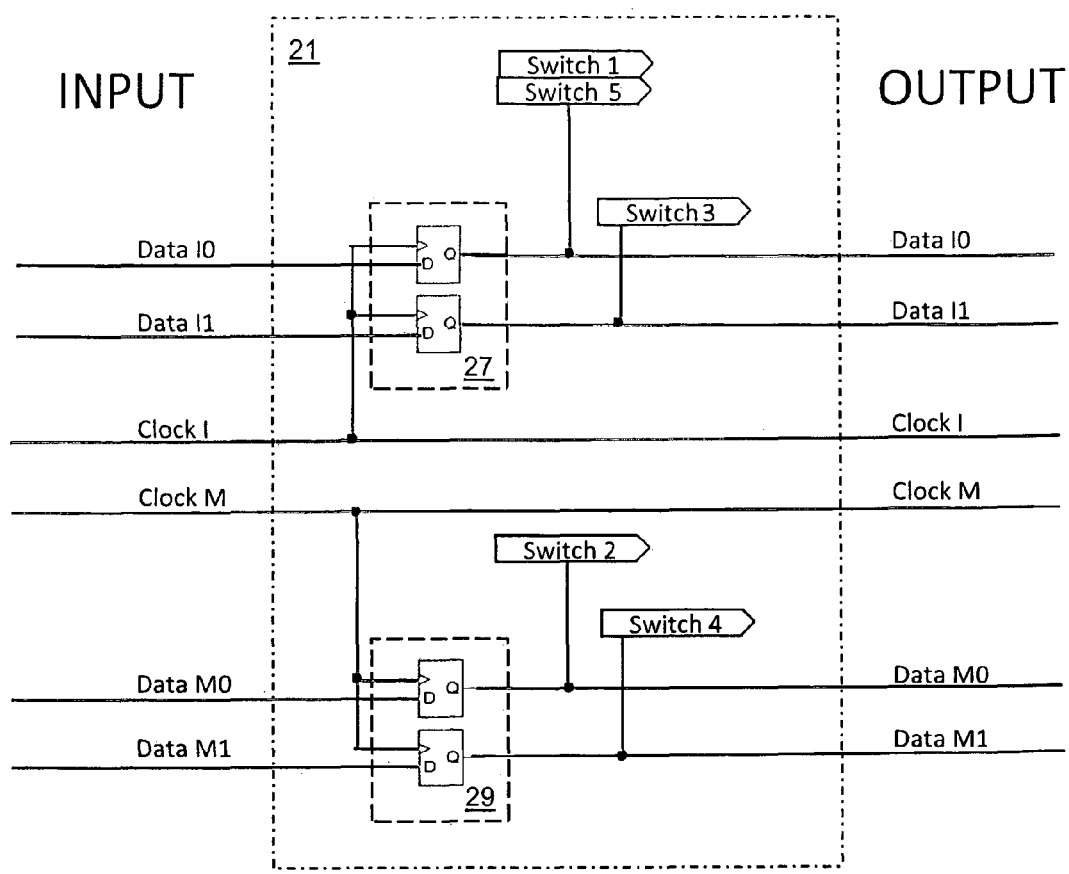
FIG. 5a illustrates schematically the switch logic unit comprising two pairs of flip-flops for controlling the switches of the current supply unit and the voltage buffer unit.

FIG. 5a shows an implementation of a switch logic unit of the invention using digital flip-flops. Two 2-bit flip-flops 27, 29 are implemented, one 2-bit flip-flop 27 determining the current injecting function of the electrodes 15, the other 2-bit flip-flop 29 determining the measurement function. Two clocks, Clock I for the current injection function and clock M for the measurement function, drive the scanning procedure at different rates (FIG. 5). Clock I can be much slower than clock M, for example 32 times slower in an arrangement with 32 electrodes. With 16 working electrodes, clock I can be 16 times slower than clock M. In case out of 32 electrodes a number n of the electrodes are not working, e.g. because of poor contact with the skin, and are therefore skipped in a measurement cycle, the frequency of clock I can be (32-n) times slower than the frequency of clock M. However, for special scanning procedures, both clocks can run at the same speed or clock I can even be faster than clock M for a short period, say a fraction of a second.

Typically, a first 2-bit flip-flop of a logic unit 21 of an electrode driver 31, e.g. first 2-bit flip-flop 27, is cascaded to a second 2-bit flip-flop on a subsequent electrode driver, so that the output of the first 2-bit flip-flop is connected to the input of the second 2-bit flip-flop. The output of the first 2-bit flip-flop is then used as the logic signal for a first given electrode driver and the output of the second 2-bit flip-flop is used as the logic signal for the subsequent second electrode driver. This way, a series of 2-bit flip-flops are daisy-chained throughout the belt to form a big shift register. Alternatively, 1-bit flip-flops, in place of the 2-bit flip-flops, may serve to create an even simpler cascaded daisy chain data propagation circuit. In a further alternative higher bit flip-flops may be used. Latches, replacing the 2-bit flip-flops may also serve to create a cascaded daisy chain data propagation circuit. Generally in place of flip-flops, the use of latches is known in the art.

In contrast to other possible implementations using shift-registers, here only one clock cycle is needed to propagate the code from one electrode to the other. One flip-flop in each electrode per code bit, cascaded to the next one, makes the present invention simple and robust.

In another embodiment, latches are used to propagate the code from electrode to electrode.

As shown in FIG. 5a two different clock cycles may be used, one for the injection modality (clock I) and the other for the measurement modality (clock M). Thus, two 2-bit flip-flops of a logic unit 21 on an electrode driver 31, i.e. first 2-bit flip-flop 27 and second 2-bit flip-flop 29, are cascaded to a third and a fourth 2-bit flip-flop on a subsequent electrode driver, so that the output of the first 2-bit flip-flop is connected to the input of the third 2-bit flip-flop and the output of the second 2-bit flip-flop is connected to the input of the fourth 2-bit flip-flop. The outputs of the first and second 2-bit flip-flop are then used as the logic signal for a first given electrode driver and the outputs of the third and fourth flip-flop are used as the logic signal for the subsequent second electrode driver. This way, two series of 2-bit flip-flops with two different clock cycles are daisy-chained throughout the belt to form a shift register. Also here other types of flip-flops or in place of flip-flops latches may be used to create a cascaded daisy chain data propagation circuit.

The flip-flop types used advantageously are edge triggered D-flip-flops and/or master slave D-flip-flops.

Figure 5B:
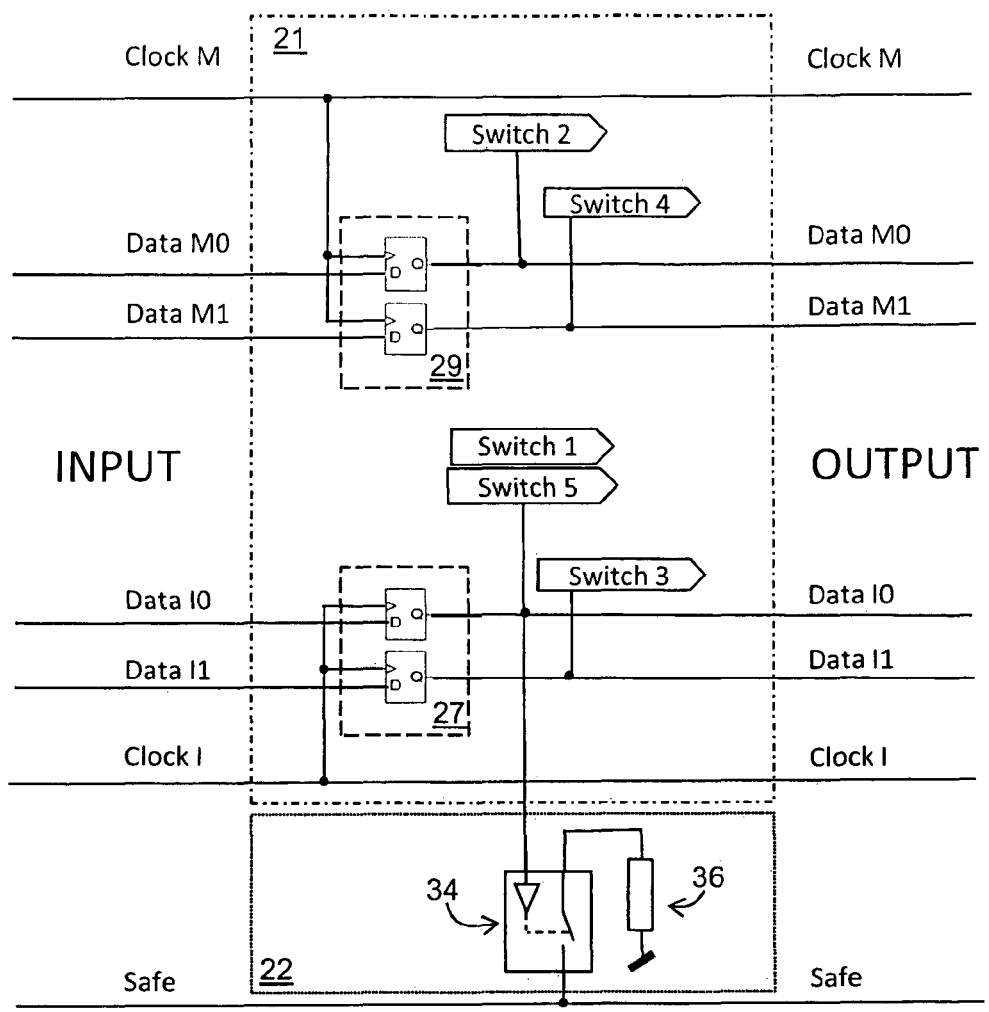
FIG. 5b illustrates schematically the switch logic unit comprising two pairs of flip-flops for controlling the switches of the current supply unit and the voltage buffer unit; furthermore schematically the safe unit in relation to the switch logic.
Figure 6A:
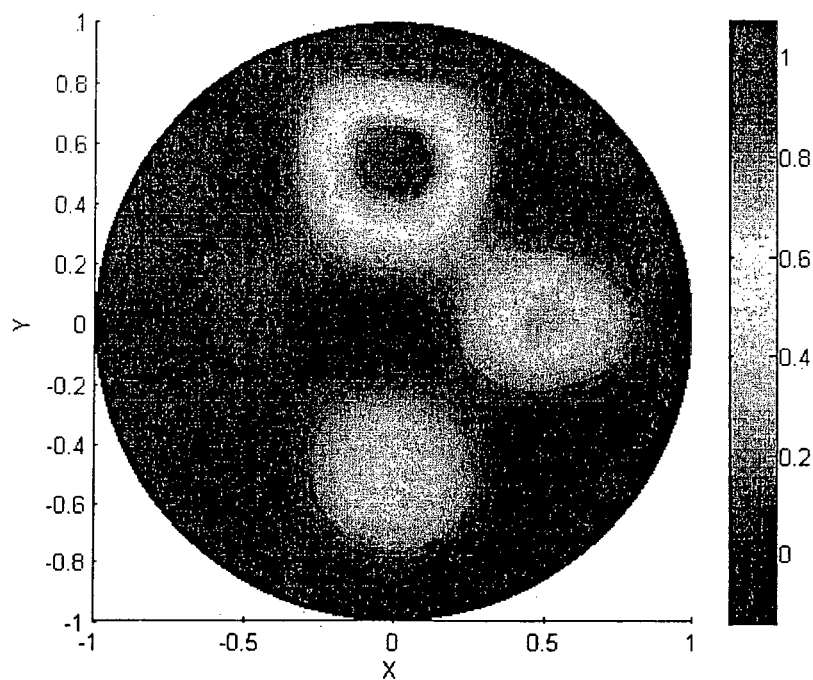
FIG. 6a illustrates an original EIT image with all electrodes functioning properly.
Figure 6B:
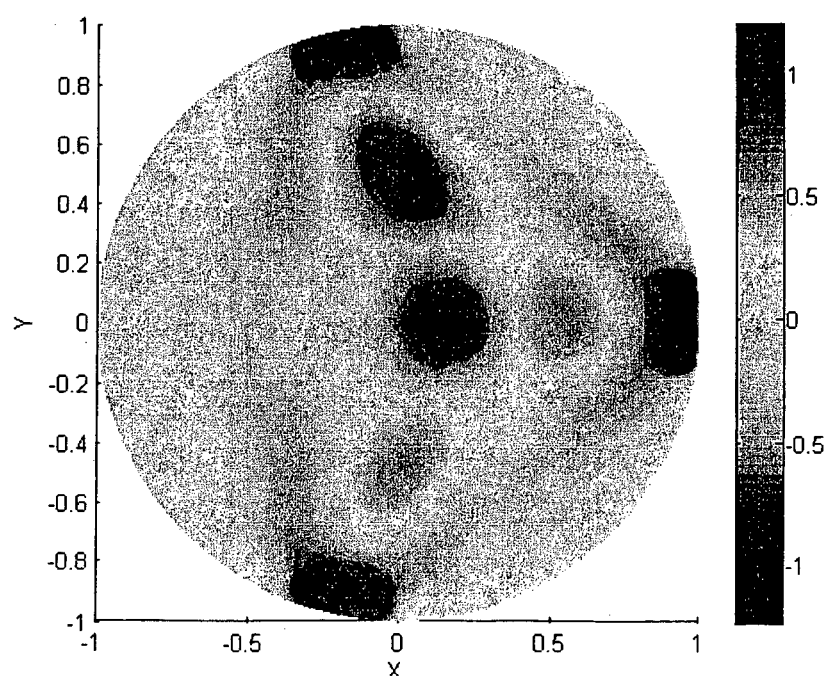
FIG. 6b illustrates an image result where electrodes 1, 10, and 24 are non-functional, electrode 1 being located at X=1, Y=0 and electrode number increasing counterclockwise.
Figure 6C:
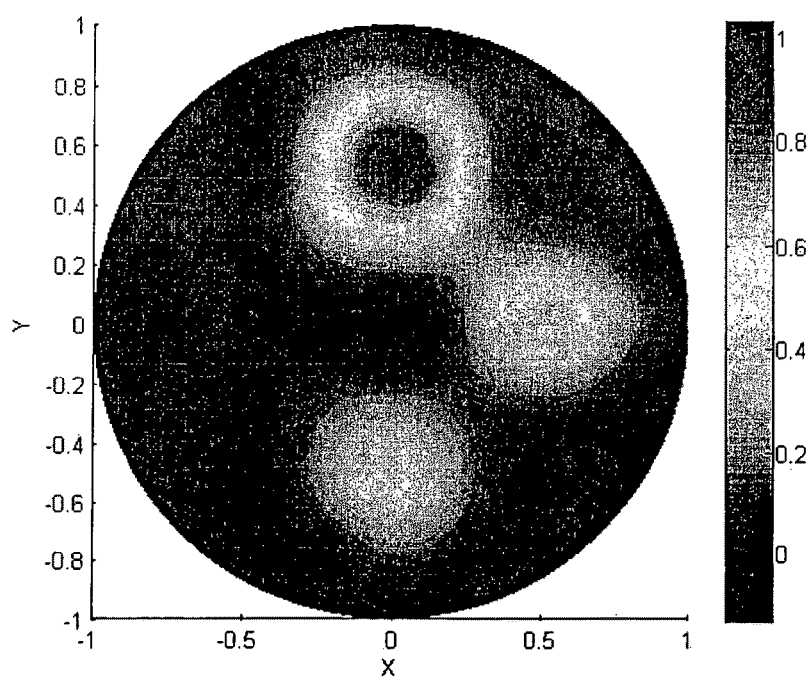
FIG. 6c illustrates a corrected image, according to present invention.
Figure 7:
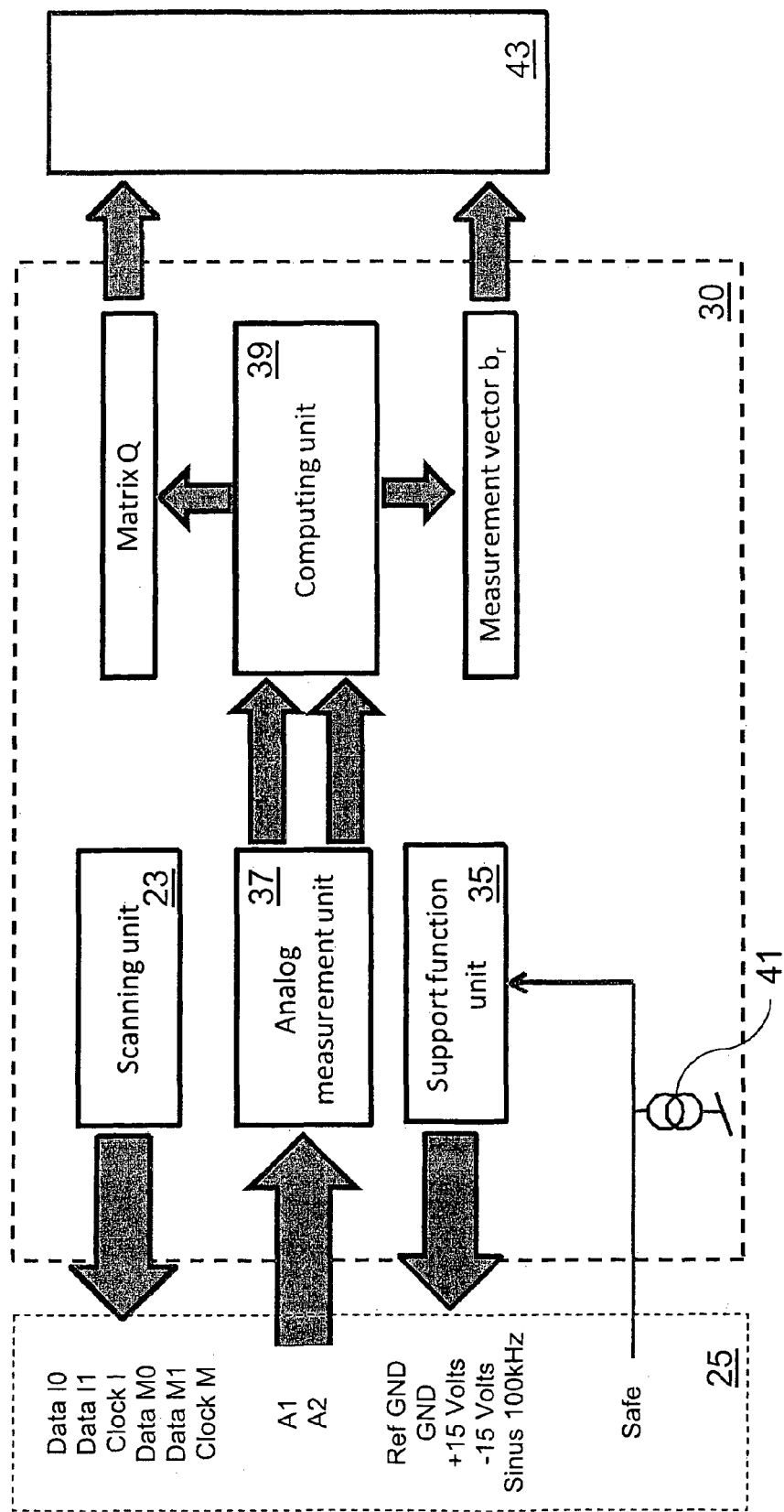
FIG. 7 illustrates the control circuit of FIG. 1 in more detail showing its principal components, namely a scanning unit, a measuring unit, a support function unit and a computing unit.

From FIGS. 1 and 7 it can be seen that the control circuit 30 drives the bus lines 25 that interconnect the electrode drivers 31. A support function unit 35 provides all supply voltages (i.e. in present exemplary embodiment consisting of two voltage supply lines and two ground lines) and the reference sinus wave to control the current supply units 17, which are operated as individual injecting current sources on each electrode 15. The line "safe" is driven by a further current source (41). If one of the electrode drivers 31 switches its on-board injecting current source to "on", the "safe" line is switched to a resistor 36 (e.g. of 1 kOhm as shown in FIG. 5b). Switch 34 and resistance 36 together form a safety unit 22 which is part of the integrated electronics 33 of the electrode drivers 31. If, by accident, several electrode drivers 31 would switch on their on-board injection current sources at the same time, the current on the "safe" line would be diverted through several respective resistors and consequently the voltage on the "safe" line would drop below a threshold value. Such condition is detected by the support function unit 35 shown in FIG. 7 which, in consequence, cuts the power supply lines to prevent excess current injection.

Figure 3:
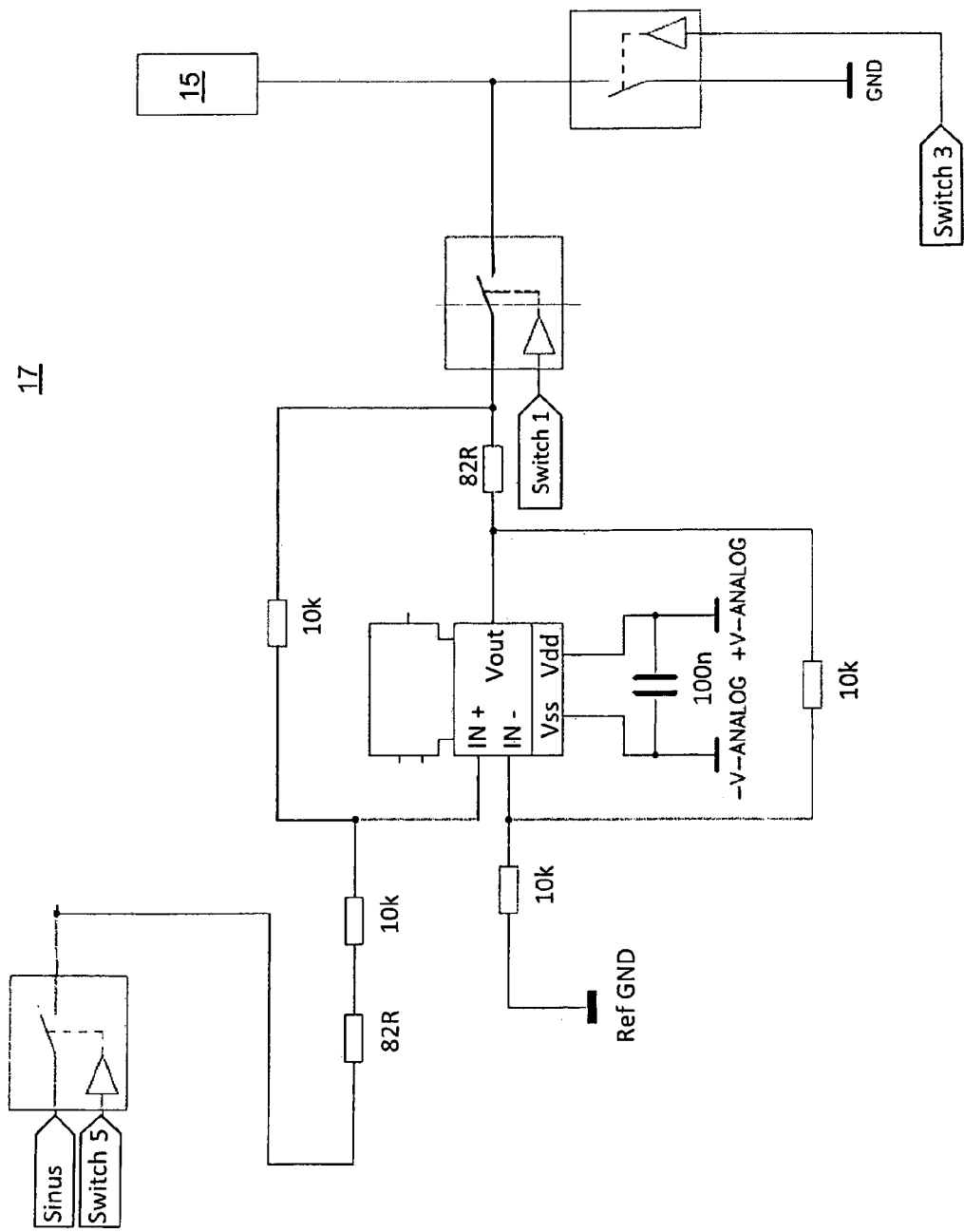
FIG. 3 illustrates the current supply unit with a set of command switches for connecting the electrode with either the current supply unit or with the reference potential.

In one embodiment, each electrode driver 31 can assume different functionalities as illustrated in Tables 1 and 2. The electrode driver 31 can act as an injecting current source, as reference potential, connect the electrode with analog bus line A1 or A2, or combine all of these functions. In FIG. 3 an implementation of the current supply unit 17 is demonstrated. This current supply unit 17 comprises a set of command switches for connecting the electrode with either the injecting current supply or with a reference potential (e.g. ground). The exemplary current supply unit 17 shown in FIG. 3 comprises resistor elements of 10 kiloohm (as indicated by 10 k) or 82 ohm (as indicated by 82R) and a capacitor with a capacitance of 100 nanofarad (as indicated by 100n). In FIG. 4 one implementation of the voltage buffer unit 19 is demonstrated. This voltage buffer unit 19 comprises first and second voltage buffers and two respective command switches for connecting the electrode buffers with analog sampling lines A1 and A2, respectively. Alternatively, the electrode driver 31 is switched so that the electrode is passive, i.e. the electrode is disconnected from all analog signal lines (i.e. A1 and A2) and the electrode.

In one embodiment of the invention, the electrode drivers 31 are controlled by a control circuit 30 which contains four functional blocks: a scanning unit 23, an analog measuring unit 37, a support function unit 35, and a computing unit 39 as depicted in FIG. 7. The scanning unit 23 prepares the two 2-bit commands for each electrode driver 31. One 2-bit command defines the current injecting function of the electrode drivers 31; the other 2-bit command defines its measurement function as shown in Tables 1 and 2.

TABLE 1

AC current injection command structure.

| Function | I0 | I1 | Switch 1 | Switch 3 | Switch 5 |
|---|---|---|---|---|---|
| NOP | 0 | 0 | Off | Off | Off |
| Current Source | 1 | 0 | On | Off | On |
| Reference Potential | 0 | 1 | Off | On | Off |

NOP means "no operation", i.e. not connected to electrode.

TABLE 2

Measurement command structure

| Function | M0 | M1 | Switch 2 | Switch 4 |
|---|---|---|---|---|
| Disconnect analog lines A1 & A2 | 0 | 0 | Off | Off |
| Connect analog line A1 to electrode | 1 | 0 | On | Off |
| Connect analog line A2 to electrode | 0 | 1 | Off | On |

The control circuit 30 moves I0, I1, M0, and M1 through the daisy chain at rates controlled by the two clock lines Clock I and Clock M. The clock rates are calculated from the desired image rate and the number of electrodes according to the following equations:

Image rate (in images per second): IR,
Number of electrodes: e,
Clock I (in Hz)=IR*e,
Clock M (in Hz)=IR*e*e.

For example, for a system with 8 electrodes 15 and an image rate of 20 images per second, the Clock I cycles at 160 Hz while Clock M cycles at 1280 Hz, provided that all electrodes 15 have the same amount of measuring time available.

A system with 32 electrodes and an image rate of 50 images per second will require a rate of 1600 Hz for clock I and 51200 Hz for clock M.

Figure 8:
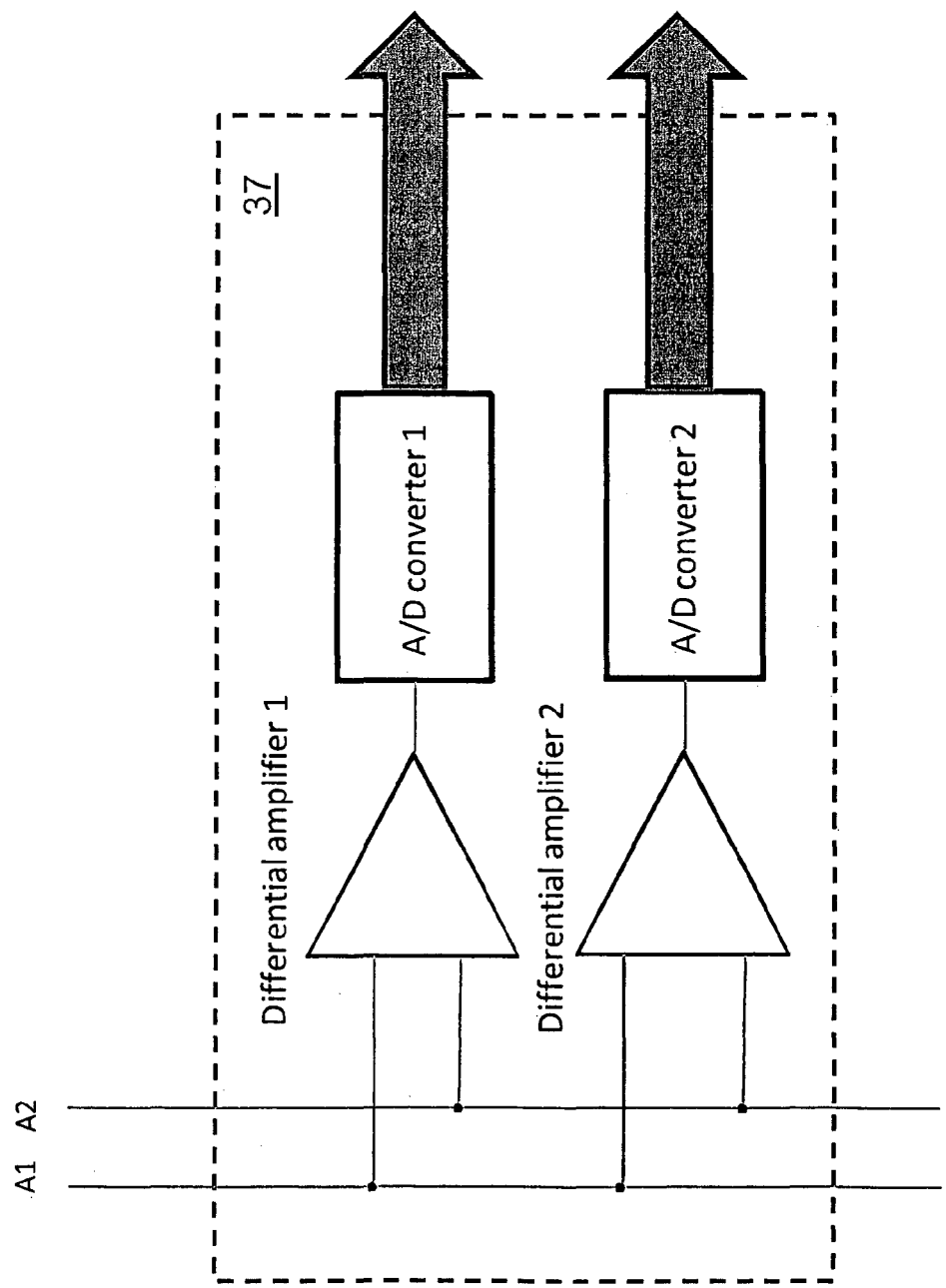
FIG. 8 illustrates the measuring unit of FIG. 7 in more detail.

In one embodiment, during each clock M cycle, the analog measurement unit 37 amplifies the difference between the two analog lines, A1 and A2, and forwards the result to a first A/D converter, e.g. a 12-bit, 10-Megasamples per second A/D converter (shown in FIG. 8). Alternatively, a more precise A/D converter could be used (e.g. 16 bits). The computing unit (39) (shown in FIG. 7) demodulates the measurement to amplitude and phase by multiplication with the excitation signal at 0 degree and at 90 degrees, as is known in the art and shown in the following paragraph:

First, for a certain measuring time, typically 20 to 100 microseconds, each sample point is multiplied with its corresponding value of the excitation signal (which was used for the current generation) and summed over the said measuring time, yielding I, the in-phase (or real) component. Similarly, for the same measuring time, each sample point is multiplied with the 90-degree phase-shifted excitation signal and summed over the said measuring time, yielding Q, the quadrature (or imaginary) component. Second, the amplitude is thereafter computed as $\sqrt{I^2+Q^2}$ and the phase difference between the measured signal as arctan $$\left(\frac{Q}{I}\right) \text{arctan}(q/i).$$

The result of the amplitude measurement is moved into the measurement vector b which is thereafter subject to modification according to the subsequently described electrode assessment.

The analog measurement unit 37 further measures the voltage on line A1 with a second A/D converter (shown in FIG. 8), which can be of the same specification as the first A/D converter described above. The computing unit 39 checks if the measurement is close to the supply voltage, typically higher than 80% of the supply voltage. If this is the case, then the corresponding electrode is tagged as potentially non-functional.

According to another aspect of the invention a safety connection is provided to prevent accidental multiple AC current injection. For this purpose, a DC current source 41 is electrically connected to all electrodes 15. This connection is called "safe" (FIGS. 5 and 7). A typical DC current is 2 mA. An additional switch (switch 6) on each electrode driver 31 connects this DC current source 41 to ground via a resistor as soon as the function of the electrode 15 is to inject AC current (FIG. 5). A typical value of this resistor is 1 kOhm. A voltmeter, for example a comparator as part of the control circuit 30, measures the resulting voltage. If one electrode 15 injects current, the voltage on the "safe" connection is e.g. 2 Volts. If more than one electrode 15 starts to inject AC current, the voltage on the "safe" connection drops to typically 1 Volt. In one embodiment, if the voltage on the "safe" connector drops below a selected threshold value between 1.1 and 1.9 Volts, or below 1.5 Volts, the comparator switches all supply lines to the electrodes 15 off and thereby prevents the injection of dangerously high AC currents.

The analog measurement unit 37 advantageously also measures the pulling force of the two arms 45, 47 of the belt 13. This may be done by a simple strain gauge. The baseline of this sensor is used to provide guidance to the user to improve electrode contact. If the force is too small, the belt is probably too loose and the electrodes 15 do not make proper contact. If the force is too high, the patient is probably restricted in his/her breathing. If the force is too high and the electrodes 15 still do not make contact, there may be another problem such as hair or very dry skin.

For every EIT image to be created, the control circuit 30 makes a complete scan using all electrodes 15 sequentially. For example, if there are 8 electrodes, such a complete scan will result in 8 measurements for each location of current injection. The said complete scan yields 8*8=64 measurements, including the measurements done at the current injecting electrode and the electrode which applies the reference potential. The first partial scan is illustrated in Table 3 with electrode 1 injecting the current and electrode 2 applying the reference potential. After 8 cycles of clock M, clock I will provide one beat and as a result, electrode 2 will become the current injecting electrode. In the next 8 cycles of Clock M, the measurements will rotate again according to Table 3. This pattern is repeated until all electrodes have served once as current injecting electrode and as reference potential. With 8 electrodes, this scanning procedure will result in 64 measurements. With 32 electrodes, the number of measurements is 1024. These measurements constitute the measurement vector b, which is created by the computing unit 39. This scanning sequence is known as adjacent-adjacent (current injection on adjacent electrodes, measurement on adjacent electrodes). It is to be noted that the inventive system is not limited to this sequence but can implement any sequential scanning configuration due to the daisy chain, which allows selecting any combination of electrodes 15.

Table 3 is an illustration of a partial scanning sequence of an 8-electrode arrangement for 20 images per second. This leaves 50 ms for a full scan, i.e. 50 ms for 64 measurements or 0.78125 ms for a single measurement. Current injection occurs at Electrode 1. The content in each cell in Table 3 indicates the state of each respective electrode at the different cycles of Clock M. The electrode acting as current source is indicated as I-source. The expression Ref–GND means that the respective electrode connects to the reference potential, for example reference ground or an alternating reference potential. NOP means "no operation".

TABLE 3

Partial scanning sequence of an 8-electrode arrangement

| Clock I cycle | Clock M cycle | Electrode 1 | Electrode 2 | Electrode 3 | Electrode 4 | Electrode 5 | Electrode 6 | Electrode 7 | Electrode 8 |
|---|---|---|---|---|---|---|---|---|---|
| #Start | #Start | NOP | NOP | NOP | NOP | NOP | NOP | NOP | NOP |
| #0 | #0 | ref-GND and connect A2 | NOP | NOP | NOP | NOP | NOP | NOP | NOP |
| #1 | #1 | 1-source and connect A1 | ref-GND and connect A2 | NOP | NOP | NOP | NOP | NOP | NOP |

TABLE 3-continued

Partial scanning sequence of an 8-electrode arrangement

| Clock I cycle | Clock M cycle | Electrode 1 | Electrode 2 | Electrode 3 | Electrode 4 | Electrode 5 | Electrode 6 | Electrode 7 | Electrode 8 |
|---|---|---|---|---|---|---|---|---|---|
| #1 | #2 | I-source | ref-GND and connect A1 | connect A2 | NOP | NOP | NOP | NOP | NOP |
| #1 | #3 | I-source | ref-GND | connect A1 | connect A2 | NOP | NOP | NOP | NOP |
| #1 | #4 | I-source | ref-GND | NOP | connect A1 | connect A2 | NOP | NOP | NOP |
| #1 | #5 | I-source | ref-GND | NOP | NOP | connect A1 | connect A2 | NOP | NOP |
| #1 | #6 | I-source | ref-GND | NOP | NOP | NOP | connect A1 | connect A2 | NOP |
| #1 | #7 | I-source | ref-GND | NOP | NOP | NOP | NOP | connect A1 | connect A2 |
| #1 | #8 | I-source and connect A2 | ref-GND | NOP | NOP | NOP | NOP | NOP | connect A1 |
| #2 | #9 | connect A1 | I-source and Connect A2 | ref-GND | NOP | NOP | NOP | NOP | NOP |

The cycles numbered with #Start and #0 of clock M are preparatory cycles. Concomitant with these two cycles of clock M, clock I issues two cycles (#Start and #0) too. Current injection starts with cycle #1 of clock I. Hereby, a current is applied between electrode 1 and electrode 2. Concomitant measurement starts with cycle #1 of clock M. While the current is applied between said electrodes, a voltage is measured between each neighboring electrode pair sequentially at least once (which is indicated by cycles #1 to #8 of clock M). Then the next electrode, i.e. electrode 2, is connected as the current injecting electrode and its further adjacent electrode, i.e. electrode 3, is connected to the reference potential as indicated by cycle #2 of clock I. A new round of eight sequential measurements starts with cycle #9 of clock M. This sequence is be repeated (not shown here) until for each adjacent electrode pair functioning as injecting electrode and respective reference potential electrode, the voltage difference between each adjacent electrode pair contacting analog lines A1 and A2, respectively, is measured at least once.

After every full scan, the computing unit 39 modifies the measurement vector b by eliminating all values that were measured by the non-functional electrodes or where the non-functional electrodes acted as current injector or reference potential. This calculation results in a vector $b_r$. The computing unit 39 further creates matrix Q, an identity matrix with all lines corresponding to measurements that are invalid due to non-functional electrodes (e.g. electrodes which are not or badly contacting or which are removed) removed. Both, $b_r$ and Q are forwarded to an image calculation device 43, for example a microprocessor, which implements the image reconstruction algorithm as described above and calculates the final image. For this purpose, the vector $b_r$ replaces b and A is pre-multiplied by Q in Equation I. The number of non-functioning electrodes may be displayed together with the force measured on the belt. If the force is below a certain threshold, the user is instructed to tighten the belt. If the force is higher than a certain threshold, the user is instructed to release the belt or to change the belt.

The optional support function unit 35 provides a control signal for the injecting current sources on the electrode drivers 31. Each electrode 15 has its own current supply unit 17 which is controlled by said signal, typically a sinus wave with a frequency between 50 and 200 kHz. The support function unit 35 also provides the computing unit 39 with information regarding the demodulation of the measurements (see above).

In another embodiment, which is not depicted in the figures, the analog bus contains three or more analog, lines. For example three analog lines allow the simultaneous measurement of three electrodes. Three analog lines also allow simultaneous measurement of two differential voltages. This is an advantage since it either permits to measure more images per second, or it permits to average the signals over a longer period of time thus improving signal-to-noise ratio. More analog lines would allow more simultaneous measurements rendering the procedure even faster.

In yet another embodiment the digital control logic of the switch logic unit 21 of each electrode 15 can be put in a state where it does not act as part of the daisy chain but simply transfers the data onto the next electrode. In this way, non-functional electrodes can virtually be excluded from the scanning procedure. In this way, the loss of an electrode can be turned into a time advantage since elimination of one electrode leaves more time for measurement on the other electrodes.

According to an embodiment of the invention, the electrode drivers 31 are integrated in an application-specific integrated circuit 33 that is mounted in close proximity of the electrode 15 and on the electrode itself.

All switches indicated in the figures are not necessarily in the unit where they appear on the Figures but may be arranged at any convenient location on the integrated circuit 33 or more generally on the electrode driver 31.

Although the present invention has been described in considerable detail and with reference to certain embodiments thereof, other embodiments are possible. Therefore, the spirit and scope of the appended claims should not be limited to the description of the versions contained therein.

The reader's attention is directed to all papers and documents which are filed concurrently with this specification and which are open to public inspection with this specification, and the contents of all such papers and documents are incorporated herein by reference. All features disclosed in this specification (including any accompanying claims, abstracts, and drawings) may be replaced by alternative features serving the same, equivalent or similar purpose, unless expressly stated otherwise. Unless expressly stated otherwise, each feature disclosed is one example only of a generic series of equivalent or similar features.

The invention claimed is:

1. An electrode assembly for an EIT scanning device, comprising:
   an electrode;
   a current supply unit;
   a voltage buffer unit;
   a switch logic unit in contact with switches for actuating the current supply unit and the voltage buffer unit in accordance with data received from the switch logic unit, the switch logic unit comprising at least one first shift register and at least one second shift register, the at least one first shift register controlled to advance a first command structure at a first interval and the at least one second shift register controlled to advance a second command structure at a second interval;
   a first plurality of lines for connecting the current supply unit and the voltage buffer unit with the electrode; and
   a second plurality of lines for connecting the current supply unit and the voltage buffer unit with the switch logic unit.

2. The electrode assembly of claim 1 wherein the at least one first shift register and the at least one second shift register are controlled by two different clocks and wherein the two different clocks comprise two different clock rates and/or clock lines.

3. The electrode assembly of claim 1 wherein the at least one first shift register and the at least one second shift register are located in close proximity to the electrode.

4. The electrode assembly of claim 1 wherein at least one of the at least one first shift register or the at least one second shift register is a flip-flop.

5. The electrode assembly of claim 1 wherein the switch logic unit comprises the at least one first shift register for connecting the current supply unit with the electrode via at least a first switch, and the at least one second shift register for connecting the voltage buffer unit with analog lines via at least a second switch.

6. The electrode assembly of claim 5 further comprising a third switch controlled by the first shift register for connecting the electrode with a reference potential, wherein the at least one first shift register is connected with the first and third switch.

7. The electrode assembly of claim 5 wherein the voltage buffer unit comprises a first and a second voltage buffer and said second switch and a fourth switch for connecting one of or both of the first and second voltage buffers to the respective first and second analog lines.

8. The electrode assembly of claim 7 wherein the at least one second shift register is connected with the second and fourth switch.

9. The electrode assembly of claim 1 further comprising an additional switch for connecting a reference signal line with the current supply unit.

10. The electrode assembly of claim 1 wherein the current supply unit, the voltage buffer unit, the shift registers and the switches are integrated in an integrated circuit, and wherein the integrated circuit is arranged on or attached to the electrode.

11. A belt-like device, comprising:
   a plurality of electrode assemblies, each electrode assembly comprising:
      an electrode;
      a current supply unit;
      a voltage buffer unit;
      a switch logic unit in contact with switches for actuating the current supply unit and the voltage buffer unit in accordance with data received from the switch logic unit, the switch logic unit comprising at least one first shift register and at least one second shift register, the at least one first shift register controlled to advance a first command structure at a first interval and the at least one second shift register controlled to advance a second command structure at a second interval;
      a first plurality of lines for connecting the current supply unit and the voltage buffer unit with the electrode; and
      a second plurality of lines for connecting the current supply unit and the voltage buffer unit with the switch logic unit;
   the plurality of electrode assemblies arranged in a spaced apart relationship on a supporting strap element, the supporting strap element comprising connecting lines for connecting the current supply units, the voltage buffer units and the switch logic units of the plurality of electrode assemblies with a control circuit.

12. The belt-like device of claim 11 wherein the switch logic units of neighboring electrode assemblies are connected in series with each other.

13. The belt-like device of claim 11, wherein the current supply units and the voltage buffer units of different electrode assemblies are connected with each other in parallel.

14. A method of measuring an EIT-image, comprising:
   using a plurality of electrode assemblies arranged in a spaced apart relationship, each electrode assembly comprising:
      an electrode;
      a current supply unit;
      a voltage buffer unit;
      a switch logic unit;
      a first plurality of lines for connecting the current supply unit and the voltage buffer unit with the electrode; and
      a second plurality of lines for connecting the current supply unit and the voltage buffer unit with the switch logic unit, the switch logic unit being in contact with switches for actuating the current supply unit and the voltage buffer unit in accordance with data received from the switch logic unit;
      the plurality of electrode assemblies connected by connecting lines for connecting the current supply units, the voltage buffer units and the switch logic units with a control circuit;
   controlling the switch logic with at least one first shift register to advance a first command structure and at least one second shift register to advance a second command structure; and
   clocking the at least one first shift register and the at least one second shift register in two different intervals in order to advance the first command structure at a first interval and the second command structure at a second interval.

15. The method of claim 14, further comprising controlling each of the first shift register and the second shift register by at least one of a different clock rate and a different clock line.

* * * * *